United States Patent [19]

Koubek et al.

[11] Patent Number: 5,545,472
[45] Date of Patent: Aug. 13, 1996

[54] WATER-BORNE, WATER REDISPERSIBLE, LAMINATING ADHESIVES FOR NONWOVEN APPLICATIONS

[75] Inventors: Timothy C. Koubek, Clinton; Paul P. Puletti, Pittstown; Joseph Wieczorek, Jr., Flemington, all of N.J.

[73] Assignee: National Starch and Chemical Investment Holding Corporation, Wilmington, Del.

[21] Appl. No.: 392,637

[22] Filed: Feb. 22, 1995

Related U.S. Application Data

[62] Division of Ser. No. 289,601, Aug. 12, 1994.

[51] Int. Cl.$^6$ ....................................... B32B 5/02
[52] U.S. Cl. ........................... 428/261; 428/286; 428/355
[58] Field of Search ..................................... 428/261, 355, 428/286; 156/181, 328, 332, 336

[56] References Cited

U.S. PATENT DOCUMENTS 5,217,798  6/1993  Brady et al. ............................. 428/246

FOREIGN PATENT DOCUMENTS 2079726  4/1993  Canada .

Primary Examiner—Jenna Davis
Attorney, Agent, or Firm—William K. Wissing

[57] ABSTRACT

A specific class of water-borne, water redispersible laminating adhesives is disclosed which is desirable for bonding nonwoven substrates to themselves or to other substrates. The adhesives provide improved bond strength and improved water redispersibility when compared to laminating adhesives currently used for the same purpose. Furthermore, the novel adhesives are much less sensitive to the presence of significant levels of plasticizer than are laminating adhesives currently used, which exhibit reduced water redispersibility when such plasticizers are present in significant amounts. The novel laminating adhesives contain an aqueous styrene/acrylic polymer dispersion prepared by radical-initiated emulsion polymerization of unsaturated monomers in the presence of starch degradation products having a weight average molecular weight range of from about 2500 to 25000 and which are obtainable by hydrolysis in the aqueous phase. The adhesives may contain only the starch-modified, styrene/acrylic polymer dispersion, or may further include other components, such as plasticizers and/or rheology modifiers, when required. The novel adhesives are particularly useful in disposable articles wherein a nonwoven substrate is bonded to a second substrate via a water-borne, laminating adhesive. The disposable articles may include an absorbent core portion disposed between and proximate the nonwoven and second substrate.

10 Claims, No Drawings

WATER-BORNE, WATER REDISPERSIBLE, LAMINATING ADHESIVES FOR NONWOVEN APPLICATIONS

This application is a division of application Ser. No. 08/289,601, filed Aug. 12, 1994 pending.

FIELD OF THE INVENTION

This invention relates to novel water-borne, water-redispersible laminating adhesives which are used in articles wherein nonwoven substrates are bon led to a second substrate, to processes for bonding nonwoven substrates and to articles comprising the novel laminating adhesives.

BACKGROUND OF THE INVENTION

A nonwoven fabric is defined as an interlocking polymer network characterized by flexibility, porosity and integrity. The individual fibers used to compose the nonwoven fabric may be synthetic, naturally occurring, or a combination of the two. The individual fibers may be mechanically, chemically, or thermally bonded to each other. Nonwovens are used commercially for a variety of applications including disposable articles such as household wipes, surgical drapes, medical dressings, diapers, adult incontinent products and sanitary napkins. Tissue paper is a material closely related to nonwoven fabric in which the individual fibers may or may not be chemically bonded to one another. As used herein, nonwoven fabric and nonwoven may be used interchangeably and are intended to include such tissue paper.

In the aforementioned applications it is necessary to adhere the nonwoven substrate to a second substrate. The second substrate may be another nonwoven of a natural or synthetic polymeric substrate, such as a cellulosic, polyester or polyolefin. A commonly employed technique to bond the substrates together is the use of a water-borne, redispersible laminating adhesive. Suitable laminating adhesives must possess adequate adhesion to the substrates involved. For nonwoven applications they must also possess good flexibility, no staining or bleed through, suitable viscosity, and bonding range in order to function on commercially available equipment.

A variety of nonwoven applications have been developed which require that the water-borne laminating adhesive demonstrate appreciable water solubility, redispersibility or sensitivity. In these situations the water-borne laminating adhesive must provide a durable bond between the nonwoven substrate and the second substrate until exposed to a predetermined condition (e.g., water), after which the adhesive would release from the substrate(s). This water releasability is a particularly desirable property in the disposable market where flushability and/or degradeability are becoming critical.

Heretofore, the adhesive of choice in such disposable applications comprised homopolymers and copolymers of vinyl acetate prepared in the presence of hydrolyzed polyvinyl alcohol. However, such polymers require the formulation of additional polyvinyl alcohol into the adhesive compositions to impart the desired water sensitivity/redispersibility to the adhesive. Furthermore, the inclusion of significant amounts of plasticizer in adhesive formulations containing such polymers tends to decrease the water redispersibility of the adhesive, especially at elevated temperatures. In applications requiring such plasticizers, this presents problems and limitations in formulating adhesives which possess both required flexibility and water redispersibility. It would be desirable, then, to develop a water-borne laminating adhesive for use in such nonwoven applications which exhibits both improved adhesion and water redispersibility over adhesives known heretofore, while at the same time providing the formulator of the adhesive with the added flexibility of utilizing plasticizers where required.

SUMMARY OF THE INVENTION

It has now been discovered that a specific class of water-borne, water redispersible laminating adhesives is desirable for bonding nonwoven substrates to other substrates. The adhesives provide improved bond strength and improved water redispersibility when compared to vinyl acetate-based, water-borne laminating adhesives currently used for the same purpose. Furthermore, the novel adhesives are much less sensitive to the presence of significant levels of plasticizer than are laminating adhesives currently used, which exhibit reduced water redispersibility when such plasticizers are present in significant amounts. Finally, the novel laminating adhesives of the present invention do not require post-polymerization addition of components such as polyvinyl alcohol to achieve desired water redispersibility.

The novel laminating adhesives comprise an aqueous polymer dispersion prepared by radical-initiated emulsion polymerization of unsaturated monomers in the presence of starch degradation products having a weight average molecular weight range of from about 2500 to 25000 and which are obtainable by hydrolysis in the aqueous phase. The adhesives may consist only of the starch-modified polymer dispersion, or may further comprise other components, such as plasticizers and/or rheology modifiers, when required.

The novel adhesives are particularly useful in disposable articles wherein a nonwoven substrate is bonded to a second substrate via a water-borne laminating adhesive. The disposable articles may include an absorbent core portion, wherein the inventive adhesives may be used as a fixative to adhere particulate absorbent material together.

DETAILED DESCRIPTION OF THE INVENTION

The adhesives of the present invention are characterized by their ability to provide a durable bond between a nonwoven substrate and a second substrate and otherwise meet the unique requirements of the application, including dry film flexibility, non-staining, machinable viscosity and later release upon exposure to water after a desired residence period, i.e., water redispersibility.

The adhesives comprise an aqueous polymer dispersion obtainable by free-radical emulsion polymerization of unsaturated monomers, which contains at least one added starch-degradation product which is obtainable by hydrolysis in the aqueous phase and which has a weight average molecular weight ($M_W$) of from 2500 to 25000. Such starch-degradation products are referred to herein as sugared starches, as opposed to roast dextrins. The aqueous polymer dispersions utilized in the adhesive compositions of the present invention and methods for making the same are discussed in detail in Canadian Patent Application 2,079,726, in the name of Wendel, et al. Exemplary polymer emulsions are available from BASF, Ludwigshafen, Germany, under the trade name Acronal DS 3446X.

The preparation of sugared starches is generally known and is described, inter alia, in Gunther Tegge, Starke und Starkederivate, Behr's Verlag, Hamburg, 1984, p. 173 and p.

220 and in EP-A 441 197. The sugared starches to be used according to the invention are preferably those whose weight average molecular weight is in the range of 4,000 to 16,000, more preferably in the range from 6500 to 13000. The sugared starches to be used according to the invention are normally completely soluble in water at room temperature, the solubility limit generally being above 50% by weight.

It is advantageous for the sugared starches to have a nonuniformity U (defined as the ratio between the weight average molecular weight $M_W$ and the number average molecular weight $M_N$; U characterizes the molecular weight distribution) in the range from 6 to 12, preferably 7 to 11, more preferably 8 to 10. Additionally, it is advantageous for the proportion by weight of the sugared starches used having molecular weight of below 1000 to be at least 10% by weight, but not more than 70% by weight, preferably from 20 to 40%, based on the total weight of starch used.

It is advisable to use sugared starches whose dextrose equivalent DE is from 5 to 40, preferably from 10 to 30, more preferably from 10 to 20. The DE value characterizes the reduction capacity, relative to the reduction capacity of anhydrous dextrose, and is determined in accordance with DIN 10308, Edition 5.71, produced by the German Standards Committee on Foodstuffs and Agricultural products. Furthermore, it is preferable to use sugared starches whose 40% strength by weight aqueous solutions nave a dynamic viscosity determined in accordance with DIN 53 019 at 25° C. and a shear gradient of 75 reciprocal seconds, of from 0.01 to 0.06, preferably from 0.015 to 0.04, more preferably from 0.02 to 0.035.

It should be noted that molecular weight data reported herein for sugared starches to be used according to the invention are based on determinations by means of gel permeation chromatography, carried out under the following conditions:

Columns: 3 steel units measuring 7.5×600 mm, filled with TSK gel G 2000 PW; G 3000 PW and G 4000PW. Mesh 5 microns.
Eluent: Distilled water
Temp.: Room Temperature
Detection: Differential refractometer (for example ERC 7511 )
Injection Volume: 20 microliter, valve (for example VICI 6-way valve)
Evaluation: Bruker Chromstat GPC software
Calibration: The calibration was carried out in the low-molecular-weight range using glucose, raffinose, maltose and maltopentose. For the higher-molecular-weight range, pululan standard having a polydispersity of <1.2 was used.

The starting starches for the preparation of the sugared starches can in principle be any native starches, such as cereal starches, for example, corn, wheat, rice or barley, tuber and root starches, for example potatoes, tapioca roots or arrow root, or sago starches.

The sugared starches can be used without any further chemical modification, apart from the extremely simple partial hydrolysis of the starting starch for their preparation. However, it is of course also possible to use them in chemically modified form, for example by etherification or esterification. This chemical modification may also have been carried out in advance on the starting starch before degradation. Esterifications are possible using both inorganic and organic acids, or anhydrides or chlorides thereof. Phosphated and acetylated degraded starches are of particular interest. The most common method of etherification is treatment with organohalogen compounds, epoxides or sulfates in aqueous alkaline solution. Particularly suitable ethers are alkyl ether, hydroxyalkyl ethers, carboxyalkyl ethers and allylethers. It is also possible to use products of the reaction with 2,3-epoxypropyltrimethylammonium chloride. Chemically unmodified sugared starched are preferred.

Suitable monomers which can be polymerized by means of free radicals include monoethylenically unsaturated monomers, such as olefins, e.g., ethylene; vinylaromatic monomers, such as styrene, α-methylstyrene, o-chlorostyrene and vinyltoluene; vinyl and vinylidene halides, such as vinyl chloride and vinylidene chloride; esters made from vinyl alcohol and monocarboxylic acids having 1 to 18 carbon atoms, such as vinyl acetate, vinyl propionate, vinyl n-butyrate, vinyl laurate and vinyl stearate; and esters made from α,β,-monoethylenically unsaturated mono-and dicarboxylic acids, preferably having 3 to 6 carbon atoms, such as acrylic acid, methacrylic acid, maleic acid, fumaric acid and itaconic acid, with alkanols generally having from 1 to 12, preferably 1 to 8, more preferably 1 to 4, carbon atoms, such as ethyl, n-butyl, isobutyl and 2-ethylhexyl acrylates and methacrylates, dimethyl maleate and n-butyl maleate. The monomers are essentially insoluble in the aqueous media and generally form the principle monomers, which normally make up a proportion of greater than 50% by weight, based on the total amount of monomers to be polymerized.

Monomers which usually give homopolymers of increased water solubility when polymerized alone are normally only copolymerized as modifying monomers in amounts of less than 50% by weight, in general from 0.5 to 20% by weight, preferably from 1 to 10% by weight, based on the total amount of monomers to be polymerized. Examples of such monomers are α,β-monoethylenically unsaturated mono- and dicarboxylic acids having 3 to 6 carbon atoms, and amides thereof, eg. acrylic acid, methacrylic acid, maleic acid, fumaric acid, itaconic acid, acrylamide and methacrylamide, furthermore vinylsulfonic acid and water-soluble salts thereof, N-vinyl formamide and N-vinyl pyrrolidone. Monomers which usually increase the internal strength of films formed by the aqueous polymer dispersion are generally likewise only copolymerizable in minor amounts, usually from 0.5 to 10% by weight, based on the total amount of monomers to be polymerized. Such monomers normally contain an epoxide, hydroxyl, N-methylol or carbonyl group or a least two nonconjugated ethylenically unsaturated double bonds. In addition to monomers containing unsaturated double bonds, it is also possible to copolymerize minor amounts, usually from 0.01 to 4% by weight, based on the monomers to be polymerized, of molecular weight regulators, such as tert-dodecyl mercaptan. Such substances are preferably added to the polymerization zone in a mixture with the monomers to be polymerized.

Preferred classes of aqueous polymer dispersions utilized in the adhesives according to the invention are those whose polymers are obtainable by free-radical emulsion polymerization of monomer mixtures which comprise from 50 to 100% by weight, based on the total weight of monomers to be polymerized, of monomers selected from the group consisting of esters of α,β-monoethylenically unsaturated carboxylic acids having from 3 to 6 carbon atoms with alkanols having 1 to 12 carbon atoms, and styrene. More preferred are polymers obtainable by free-radical emulsion polymerization of monomer mixtures which comprise from 90 to 99% by weight, based on the total weight of monomers to be polymerized, of monomers selected from the group consisting of esters of acrylic and/or methacrylic acids and alkanols having 1 to 8 carbon atoms and styrene, and 1 to 10 weight percent, based on the total weight of monomers to be polymerized, of monomers selected from the group consisting of $\alpha,\beta$-monoethylenically unsaturated mono- and dicarboxylic acids having 3 to 6 carbon atoms, and amides thereof, preferably acrylic and methacrylic acids and amides thereof.

The aqueous polymer dispersions utilized in the inventive laminating adhesives are preferably prepared by polymerizing the monomers by the free-radical aqueous emulsion polymerization process in the presence of the sugared starches to be used in accordance with this invention. The emulsion polymerization temperature is generally from 30 to 95° C., preferably from 75 to 90° C. The polymerization medium may either comprise water alone or a mixture of water and water-miscible liquids, such as methanol. It is preferred to use water alone. The emulsion polymerization can be carried out either as a batch process or in the form of a feed process, including a step or gradient procedure. Preference is given to the feed process, in which part of the polymerization batch is heated to the polymerization temperature and partially polymerized, and the remainder of the polymerization batch is subsequently fed to the polymerization zone continuously, in steps or with superposition of a concentration gradient, usually via a plurality of spatially separate feed streams, of which one or more contain the monomers in pure or emulsified form, while maintaining the polymerization. Advantageously, the initially introduced mixture and/or the monomer feed stream contains small amounts of emulsifiers, generally less than 0.5% by weight, based on the total amount of monomers to be polymerized, in order to reduce the surface tension of the dispersion medium and thus to simplify stirring. The monomers are therefore frequently fed to the polymerization zone after pre-emulsification with these assistant emulsifiers. Due to the high water solubility of the sugared starches to be used, the feed processes can be designed in a particularly simple manner by initially introducing all of the sugared starch to be used in dissolved form in an aqueous mixture; pregelling is unnecessary. This means that the aqueous solution produced on partial hydrolysis of the starting starch can, after the hydrolysis has been terminated, for example by neutralization of the catalytic acid and cooling, be further used directly for the aqueous emulsion polymerization. Prior isolation, for example by spray drying, of the sugared starch is unnecessary.

Suitable free-radical polymerization initiators are all those which are capable of initiating a free-radical aqueous emulsion polymerization. These may be either peroxides, for example alkali metal peroxydisulfates or $H_2O_2$, or azo compounds.

Also suitable are combined systems comprising at least one organic reducing agent and at least one peroxide and/or hydroperoxide, e.g., tert-butyl hydroperoxide and the sodium metal salt of hydroxymethanesulfinic acid or hydrogen peroxide and ascorbic acid. Also suitable are combined systems additionally containing a small amount of a metal compound which is soluble in the polymerization medium and whose metallic component can exist in more than one oxidation state, where ascorbic acid is also frequently replaced by the sodium metal salt of hydroxymethanesulfinic acid, sodium sulfite, sodium hydrogen sulfite or sodium metal bisulfite and hydrogen peroxide is frequently replaced by tert-butyl hydroperoxide or alkali metal peroxydisulfates and/or ammonium peroxydisulfates. In general, the amount of free-radical initiator systems employed is from 0.1 to 2% by weight, based on the total amount of the monomers to be polymerized. Particularly preferred initiators are ammonium and/or alkali metal peroxydisulfates, alone or as a constituent of combined systems. Particularly preferred are sodium peroxydisulfates.

Particularly preferred polymer dispersions are obtainable by free-radical aqueous polymerization of monomer mixtures comprising from 40 to 85% by weight of at least one ester of $\alpha,\beta$-monoethylenically unsaturated mono-and dicarboxylic acids having from 3 to 6 carbon atoms with alkanols having 1 to 6 carbon atoms, from 15 to 60% by weight of styrene, and from 1 to 10% by weight of one or more monomers selected from the group consisting of $\alpha,\beta$-monoethylenically unsaturated carboxylic acids having 3 to 6 carbon atoms. The dispersions contain based on the weight of polymerized monomers, from 1 to 120% by weight, preferably from 10 to 65% by weight, of at least one added sugared starch. Most preferred are polymer dispersions prepared by free-radical emulsion polymerization of monomer mixtures comprising from 74 to 84% by weight of butyl acrylate, 15 to 20% by weight of styrene and 1 to 10% by weight of acrylic acid, and from 15 to 55% by weight, of at least one added starch, all weights based on the total amount of monomers to be polymerized.

The polymer dispersions prepared via free-radical emulsion polymerization may be incorporated into the inventive adhesives without further treatment. Alternately, the polymer dispersion prepared via free-radical emulsion polymerization may be converted to a redispersible powder by methods known to one skilled in the art, such as spray drying, roll drying or suction-filter drying. The powder then may be redispersed in water to form a polymer dispersion for incorporation into the inventive adhesives. Preferably the total solids content of the polymer dispersion will be from 10 to 75% by weight, more preferably from 40 to 60% by weight, based on the total weight of the polymer dispersion.

The laminating adhesive compositions may further comprise a plasticizer to modify the flexibility of the dried adhesive film. In fact, when required, higher levels of plasticizer may be incorporated into the inventive adhesive composition without detrimentally affecting the water redispersibility of the dried adhesive film, when compared to adhesives currently being used in similar applications. Accordingly, one would have more freedom in formulating laminating adhesives as claimed herein with respect to both acceptable film flexibility and water redispersibility. Representative plasticizers include acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ester, tributoxyethyl phthalate, triethylene glycol polyester of benzoic acid and phthalic acid, or mixtures thereof. Of these plasticizers, dibenzoate types are preferred. One particular plasticizer which may be used is available from Velsicol Chemical Corporation, Rosemont, Ill., under the trade name Benzoflex® 50. While the adhesive composition need not include any plasticizer, the plasticizer is generally used in amounts of 2 to 30 weight percent, preferably 5 to 20 weight percent, based on the total weight of the adhesive composition.

Other additives traditionally used in laminating adhesives may also be utilized herein in conventional amounts. Such additives include defoamers, preservatives, rheology modifiers such as thickeners or diluents, fillers, tackifiers, colorants such as dyes or pigments, and the like. Suitable rheology modifiers include, for example, starch, oliginates, bentonite, casein, fumed silica, guar gum, xanthan gum, gum tragacanth, polyvinyl alcohol, hydroxyethylcellulose, locust bean gum, methylcellulose, and the like. One preferred rheology modifier is available from Alco Chemical Corporation, Chattanooga, Tenn., under the trade name Alcogum® 296W. Useful fillers include, for example, bentonite, calcium carbonate, calcium silicate, clay, mica, silica, talc, and the like. One suitable defoamer is available from Henkel Corporation, Kankakee, Ill., under the trade name Foamaster B. A suitable preservative is available from Merck & Company, Inc., Rahway, N.J., under the trade name Tektamer 38 A.D.

In certain embodiments it may be desirable to add to the adhesive a surfactant at conventional levels. The surfactant can be anionic, cationic, amphoteric or nonionic surface-active compounds or mixtures thereof. Suitable anionic emulsifiers include, for example, alkyl sulfonates, alkylaryl sulfonates, alkyl sulfates, sulfates of hydroxyalkanols, alkyl and alkylaryl disulfonates, and the like. Suitable cationic emulsifiers include, for example, alkyl quaternary ammonium salts and alkyl quaternary phosphonium salts. Examples of suitable nonionic emulsifiers are the addition products of 5 to 50 moles of ethylene oxide adducted to straight-chain and branched-chain alkanols with 6 to 22 carbon atoms, or alkylphenols, and the like.

The novel water-borne laminating adhesives are used in the construction of articles wherein a first, nonwoven substrate is bonded to a second substrate. The second substrate may be another nonwoven substrate which is compositionally the same as or different from the first nonwoven substrate, a woven substrate, or a sheet of a thermoplastic resin prepared by methods known to those skilled in the art, such as extrusion, lamination and the like. The second substrate may be either water permeable or water impermeable, depending on the particular application. The first nonwoven and second substrates may be prepared from natural or synthetic polymeric materials. Natural polymeric substrates include, without limitation, cellulosic substrates prepared from, for example, wood pulp (such as paper) and cotton fibers (such as cloth, sheeting and industrial fabric). Synthetic polymeric substrates include, without limitation, polyester or polyolefin substrates prepared from, for example, polyethylene and polypropylene. In addition, other biodegradable polymeric materials such as polyvinyl alcohol, polyhydroxy valerate butyrate and polylactides may be used.

The articles may include an absorbent core portion. The absorbent core portion may comprise naturally occurring polymeric material, such as cellulosic absorbent material, i.e., wood pulp and/or paper, or high performance superabsorbent synthetic polymeric materials, such as polyacrylates, methacrylic acid and alkyl esters of acrylic and methacrylic acids. The absorbent core portion may be in the form of a sheet or may comprise particulate absorbent material, wherein the particles of absorbent material are adhered together by the inventive laminating adhesives. The absorbent core portion may comprise the first nonwoven substrate, in which case it is bonded to the second substrate with the inventive adhesives. Preferably, the absorbent core portion is disposed between and proximate the first nonwoven substrate and the second substrate and may be bonded to either the first nonwoven substrate or the second substrate.

Typical articles utilizing the novel laminating adhesives include, without limitation, household wipes, surgical drapes, medical dressings, disposable diapers, adult incontinent products, tampons and sanitary napkins. The use of the novel adhesives is particularly advantageous in nonwoven/nonwoven, (i.e., tissue/tissue) bonding of flushable paper products, such as toilet tissue, and disposable diapers, where water sensitivity at relatively low temperature is desirable so as to provide release from the various substrates to facilitate flushability of all or a portion of the diaper.

The adhesive can be applied to either the nonwoven substrate or to the second substrate by a variety of methods in an amount sufficient to cause the substrates to adhere one to the other. Conventional methods of applying the adhesives to the substrates are generally known or readily available to one skilled in the art and include, for example, spray coating, roll coating, extrusion coating, laminating, dipping, and the like.

The following examples, which in no way are intended to limit the scope of the claims appended hereto, illustrate the production and performance of suitable water-borne, water redispersible laminating adhesives. In the examples, all parts are by weight and all temperatures in degree Celsius unless otherwise noted.

ADHESIVE FORMULATION

EXAMPLE 1

Inventive adhesive composition Example 1 was prepared by blending together 82.4% of Acronal 3446 polymer dispersion (50% solids), 15% of Benzoflex 50 plasticizer, 2% of Alcogum 296W thickener, 0.17% Foamaster B defoamer and 0.46% Tektamer 38 A.D. preservative.

EXAMPLE 2

Comparative adhesive composition Example 2 was prepared by blending together 53.79% of a polyvinyl alcohol-modified polyvinyl acetate polymer dispersion (50% solids) with 32.15% of water, 10.75% of Benzoflex 50, 2.68% of polyvinyl alcohol, 0.13% of Foamaster B and 0.5% of Tektamer 38 A.D.

EXAMPLE 3

Inventive adhesive Example 3 comprises 100% of Acronal 3446 polymer dispersion (50% solids).

EXAMPLE 4

Comparative adhesive composition Example 4 was prepared by blending together 60.16% of a polyvinyl alcohol-modified polyvinyl acetate polymer dispersion (50% solids) with 36.13% of water, 3.00% polyvinyl alcohol, 0.14% of Foamaster B and 0.58% of Tektamer 38 A.D.

The Examples were tested for water redispersibility and subjective adhesion according to the procedures set forth below.

TEST PROCEDURES

Subjective Adhesion

A first nonwoven (tissue) substrate was bonded to a second nonwoven (tissue) substrate using the adhesives of Examples 1 and 2, respectively: Additionally, a first nonwoven substrate (spun-bound polypropylene) was bonded to a second textured polypropylene film substrate which had been treated to impart a degree of hydrophilicity thereto. The bonded substrates were allowed to dry thoroughly at ambient conditions. The bonded, dried substrates then were subjectively evaluated by physically pulling the substrates apart and noting the ease of separation of the bonded substrates.

In each case, the respective substrates bonded with the inventive adhesive Example 1 exhibited greater adhesion, i.e., were more difficult to separate, than those substrates bonded with comparative adhesive Example 2.

Water Redispersibility

Duplicate wet samples of the adhesive to be tested were coated onto release paper with a 3.0 mil bird applicator and dried overnight at room temperature. The samples were removed and accurately weighed. A 60 mesh screen was cut into 3 inch×3 inch squares and the squares were also accurately weighed.

The adhesive Examples 1–4 were placed in an Osterizer® blender with 350 ml of water at temperatures of 10° C. and 70° C. respectively. Additionally, the adhesive Example 2 was tested at 27° C. in the same manner. A few drops of defoamer were added. The cover was placed on the blender and the blender run for 10 minutes at high speed.

Following the high speed agitation, the water dispersion and any remaining lumps of adhesive were decanted from the blender, through the 60 mesh screen, into a beaker. The lumps of adhesive remained on the screen, while the dispersed materials flowed through the 60 mesh screen. A wash bottle was used to rinse the inside of the blender to remove any remaining pieces of adhesive.

The screen containing any remaining adhesive was placed in an oven (49° C.) overnight. The screen was removed from the oven, allowed to cool and again accurately weighed. The percentage of adhesive dispersed was calculated based on the initial weight of adhesive and final weight of the adhesive retained on the 60 mesh screen as follows:

% redispersed adhesive=(i-f)/i×100 i=initial dry weight of adhesive applied f=dry weight of adhesive retained on 60 mesh screen At 10° C., the % redispersed adhesive for Examples 1–4 was 99.3, 93.4, 97.6 and 97.2, respectively. At 27° C. the % redispersed adhesive for Example 2 was 82.4. At 70° C., the % redispersed adhesive for Examples 1–4 was 94.1, 47.7, 99.8 and 93.3, respectively. The results clearly indicate that the inclusion of plasticizer in the vinyl acetate-based adhesive at significant levels, for example 10% based on total weight of the adhesive, detrimentally affects the water redispersibility of the adhesive as the temperature of the aqueous media is increased. The water redispersibility of inventive adhesive Example 1 and Examples 3 and 4 (0% plasticizer) were unaffected by the increase in temperature. Therefore, at temperatures where water redispersibility is essential, for example greater than about 15° C. the inventive adhesives clearly show improved water redispersibility in the presence of plasticizers.

We claim:

1. A disposable, absorbent article of manufacture, comprising:

a first nonwoven substrate bonded to a second substrate via a water-borne, water redispersible laminating adhesive, said laminating adhesive comprising an aqueous polymer dispersion prepared by radical-initiated emulsion polymerization of a mixture of unsaturated monomers in the presence of starch degradation products having a weight average molecular weight range of from 2500 to 25,000 and which are obtainable by hydrolysis in an aqueous phase; and 2 to 30 weight percent of a plasticizer, wherein the first nonwoven substrate and the second substrate comprises polymeric materials selected from the group consisting of natural and synthetic polymeric materials and wherein, at a water-temperature of greater than about 15° C., the adhesive exhibits water redispersibility of at least about 90 percent.

2. A disposable, absorbent article of manufacture, comprising:

a first nonwoven substrate bonded to a second substrate via a water-borne, water redispersible laminating adhesive, said laminating adhesive comprising an aqueous polymer dispersion prepared by radical-initiated emulsion polymerization of a mixture of unsaturated monomers in the presence of starch degradation products having a weight average molecular weight range of from 2500 to 25,000 and which are obtainable by hydrolysis in an aqueous phase; and 2 to 30 weight percent of a plasticizer selected from the group consisting of acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ester, tributoxyethyl phthalate, triethylene glycol polyester of benzoic acid and phthalic acid.

3. The article of claim 1 or 2 wherein the second substrate is a nonwoven substrate which is compositionally the same as or different than the first nonwoven substrate.

4. The article of claim 3 wherein the first nonwoven substrate and the second nonwoven substrate comprise tissue.

5. The article of claim 4 comprising a multi-ply tissue.

6. The article of claim 1 or 2 further comprising an absorbent core portion disposed between and proximate the first nonwoven substrate and the second substrate.

7. The article of claim 6 comprising a disposable diaper.

8. The article of claim 6 wherein the absorbent core portion comprises particulate absorbent material adhered together by the laminating adhesive.

9. The article of claim 1 or 2 wherein the first nonwoven substrate comprises an absorbent core portion.

10. The article of claim 9 wherein the absorbent core portion comprises particulate absorbent material adhered together by the laminating adhesive.

\* \* \* \* \*